United States Patent [19]

Takeshita et al.

[11] Patent Number: 5,116,985

[45] Date of Patent: May 26, 1992

[54] ISOQUINOLINE DERIVATIVES AND SALTS THEREOF

[75] Inventors: Yasuyoshi Takeshita, Tochigi; Hiroshi Nakamura, Chiba; Susumu Ishiguro, Saitama; Noboru Kwaguchi, Tochigi; Shin'ichi Shimada, Tochigi; Tadayoshi Koyama, Tochigi; Motohide Seya, Tochigi; Noriko Abe, Tochigi; Shin Nomoto, Tochigi, all of Japan

[73] Assignee: Snow Brand Milk Products Co., Ltd., Hokkaido, Japan

[21] Appl. No.: 630,064

[22] Filed: Dec. 19, 1990

[30] Foreign Application Priority Data

Dec. 28, 1989 [JP] Japan .................................. 1-342737
Jun. 8, 1990 [JP] Japan .................................. 2-150483
Oct. 18, 1990 [JP] Japan .................................. 2-280262

[51] Int. Cl.$^5$ .................. C07D 217/02; C07D 217/16; C07D 217/24; C07D 217/26
[52] U.S. Cl. .................................. 546/141; 546/145; 546/146; 546/147
[58] Field of Search ................. 546/141, 145, 146, 147

[56] References Cited

U.S. PATENT DOCUMENTS

| | | | |
|---|---|---|---|
| 2,538,341 | 1/1951 | Ullyot | 546/141 |
| 4,021,478 | 5/1977 | White | 260/515 |
| 4,241,209 | 12/1980 | Sommer et al. | 546/147 |
| 4,520,025 | 5/1985 | Campbell et al. | 546/145 |
| 4,673,745 | 6/1987 | Sommer et al. | 546/147 |

FOREIGN PATENT DOCUMENTS 48433 3/1982 European Pat. Off. .

OTHER PUBLICATIONS

Georgian et al., "Chemical Abstracts", vol. 58, 1963, col. 4515e.
Journal of Organic Chemistry vol. 27 No. 12 pp. 4571-1479 Dec. 12, 1962 Chemical Abstracts vol. 97 No. 1 p. 569 5th Jul. 1982.

Primary Examiner—C. Warren Ivy
Assistant Examiner—James H. Turnipseed
Attorney, Agent, or Firm—Burgess, Ryan & Wayne

[57] ABSTRACT

The invention provides novel compounds and salts thereof, have the structure

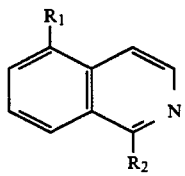

wherein $R_1$ is a guianidinobenzoyloxy group and $R_2$ is a hydrogen atom, a hydroxy, cyano, —$COR_3$ (wherein $R_3$ is an amino or lower alkyl group) or —$COOR_4$ group [wherein $R_4$ is a hydrogen atom, lower alkyl, phenyl, benzyl or —$CH_2CONR_5R_6$ group (wherein $R_5$ and $R_6$ are the same or different and selected from a hydrogen atom and lower alkyl groups)], and wherein $R_1$ is a hydroxy group and $R_2$ is a —$COR_3$ (wherein $R_3$ is an amino or lower alkyl group) or —$COOR_4$ group [wherein $R_4$ is a ($C_1$, $C_3$ or $C_4$) alkyl, phenyl, benzyl or —$CH_2CONR_5R_6$ group (wherein $R_5$ and $R_6$ are the same or different and selected from a hydrogen atom and lower alkyl groups)]. The compounds, wherein $R_1$ is a guanidinobenzoyloxy group, are useful protease inhibitors as anti-trypsin agents.

20 Claims, No Drawings

ISOQUINOLINE DERIVATIVES AND SALTS THEREOF

BACKGROUND OF THE INVENTION

The present invention relates to novel isoquinoline derivatives and pharmaceutically acceptable salts thereof. More specifically, the present invention relates to isoquinolyl guanidinobenzoate derivatives and they have application as protease inhibitors, in particular as antitrypsin agents. Furthermore, most of 5-hydroxyisoquinoline derivatives described in this invention, are new compounds and are useful as intermediates for the preparation of the isoquinolyl guanidinobenzoate derivatives.

JP No. 2107/74, U.S. Pat. No. 3,751,447 and Ger. Pat. No. 2050484 claim a series of guanidinocaproate. JP No. 1063/86, Eur. Pat. No. 48433 and U.S. Pat. No. 4,454,338 claim a series of guanidinobenzoate as useful protease inhibitors and anti-complementary agents. JP No. 89640/77, Ger. Pat. No. 2548886 and U.S. Pat. No. 4,021,472 claim a series of guanidinobenzoates as useful protease inhibitors.

SUMMARY OF THE INVENTION

It has now been discovered that novel compounds of the formula (I)

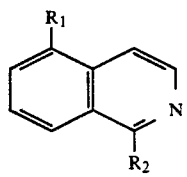

(I)

and pharmaceutically acceptable salts thereof wherein $R_1$ is

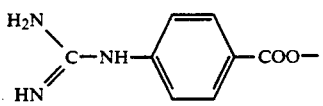

and $R_2$ is a hydrogen atom, a hydroxy, cyano, —$COR_3$ (wherein $R_3$ is an amino or ($C_1$-$C_4$) alkyl group) or —$COOR_4$ group [wherein $R_4$ is a hydrogen atom, a ($C_1$-$C_4$) alkyl, phenyl, benzyl or —$CH_2CONR_5R_6$ group (wherein $R_5$ and $R_6$ are the same or different and selected from a hydrogen atom and ($C_1$-$C_4$) alkyl groups)].

These isoquinolyl guanidinobenzoate derivatives are excellent inhibitors against proteases and especially useful as anti-trypsin agents.

Furthermore, the compounds of the formula (I), wherein $R_1$ is a hydroxy group and $R_2$ is a —$COR_3$ (wherein $R_3$ is an amino or ($C_1$-$C_4$) alkyl group) or —$COOR_4$ group [wherein $R_4$ is a ($C_1$, $C_3$ or $C_4$) alkyl, phenyl, benzyl or —$CH_2CONR_5R_6$ group (wherein $R_5$ and $R_6$ are the same or different and selected from a hydrogen atom and ($C_1$-$C_4$) alkyl groups)], are useful intermediates for the preparation of the isoquinolyl guanidinobenzoate derivatives.

DETAILED DESCRIPTION OF THE INVENTION

As illustrative examples of "($C_1$-$C_4$) alkyl groups", there may be mentioned methyl, ethyl, propyl, isopropyl, butyl, isobutyl, sec-butyl and tert-butyl.

The isoquinoline derivatives of the present invention are synthesized as shown in FIG. 1. The numerals in the parentheses show the compound numbers of isoquinoline derivatives of the present invention.

The isoquinolyl guanidinobenzoate derivatives of the formula (II) of the present invention can be prepared by a reaction of 4-guanidinobenzoic acid or a reactive derivative thereof and a 5-hydroxyisoquinoline derivative of the formula (III) or a reactive derivative thereof:

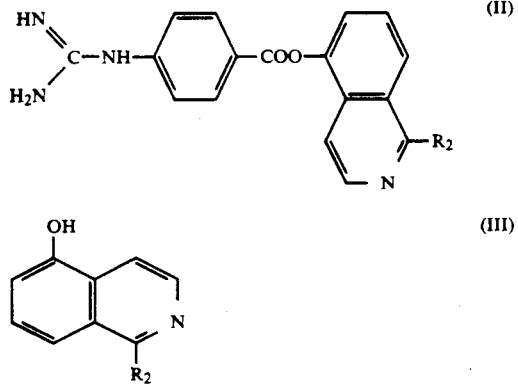

wherein $R_2$ is a hydrogen atom, a hydroxy, cyano, —$COR_3$ (wherein $R_3$ is an amino or ($C_1$–$C_4$) alkyl group) or —$COOR_4$ group [wherein $R_4$ is a hydrogen atom, a ($C_1$–$C_4$) alkyl, phenyl, benzyl or —$CH_2CONR_5R_6$ group (wherein $R_5$ and $R_6$ are the same or different and selected from a hydrogen atom and ($C_1$–$C_4$) alkyl groups)].

The reaction of 4-guanidinobenzoic acid and a 5-hydroxyisoquinoline derivative (III) can be performed by an application of conventional coupling reaction.

METHOD A-1

Compounds (II) of the present invention can be prepared by a reaction of 4-guanidinobenzoic acid or a salt thereof with a 5-hydroxyisoquinoline derivative (III) or a salt thereof in the presence of a catalyst or a condensing agent, followed by removal of the protective groups as required. Suitable examples of the acidic catalysts are sulfuric acid, hydrochloric acid, p-toluenesulfonic acid, phosphorous oxychloride, polyphosphoric acid and boron trifluoride. And suitable examples of the condensing agents are diphenylphosphorylazide, dicyclohexylcarbodiimide (DCC), N,N'-carbodiimidazole, N,N'-disuccinimidyl carbonate, 1-(3-dimethylaminopropyl)-3-ethylcarbodiimide, dimethylformamide, diethylacetal, N,N'-dimethylphosphoramidic dichloride and phenyl dichlorophosphate. Additionally the basic catalysts, e.g. pyridine, triethylamine, diisopropylethylamine, ditert-butylamine, dimethylaminopyridine, pyrrolidinopyridine, N-methylmorpholine and 1,8-diazabicyclo[5,4,0]-7-undecene may be used with above condensing agents.

The solvent can be selected, according to the reaction conditions, from pyridine, dimethylformamide, chloroform, dichloromethane, carbon tetrachloride, benzene, toluene, xylene, diethyl ether, dioxane, tetrahydrofuran, acetonitrile, ethyl acetate, dimethylsulfoxide and water. As an example of method A-1, 4-guanidinobenzoic acid and a 5-hydroxyisoquinoline derivative (III) are allowed to react in the presence of DCC in pyridine. The reaction is carried out at −30° to 100° C. for a few hours to several days.

METHOD A-2

Compounds (II) of the present invention can be prepared by a reaction of a reactive derivative of 4-guanidinobenzoic acid or a salt thereof, and a 5-hydroxyisoquinoline derivative (III) or a salt thereof, followed by removal of the protective groups as required.

The reactive derivativers of 4-guanidinobenzoic acid include acid halides (e.g. acid chloride and acid bromide), an acid anhydride, mixed acid anhydrides with other acids (e.g. trichloroacetic acid, methanesulfonic acid, benzenesulfonic acid and isobutoxyformic acid), onium salts (e.g. 2-bromo-1-pyridinium iodide, 2-chloro-3,5-dinitropyridine and 2-chloro-1-methylpyridinium iodide) or active esters (e.g. p-nitrophenyl ester and N-hydroxysuccinimide ester).

Additionally the basic catalysts, e.g. pyridine, triethylamine, diisopropylethylamine, di-tert-butylamine, dimethylaminopyridine, pyrrolidinopyridine, N-methylmorpholine and 1,8-diazabicyclo[5,4,0]-7-undecene, can be used as required.

The solvent can be used, according to the reaction conditions, from pyridine, chloroform, dichloromethane, carbon tetrachloride, benzene, toluene, xylene, diethyl ether, dioxane, tetrahydrofuran, acetonitrile and dimethylsulfoxide.

As an example of method A-2, 4-guanidinobenzoyl chloride and a 5-hydroxyisoquinoline derivative (III) are allowed to react in pyridine at −30° to 100° C. for a few hours to several days.

METHOD A-3

Compounds (II) of the present invention can be prepared by a reaction of 4-guanidinobenzoic acid and a reactive derivative of Compound (III), followed by removal of the protective groups as required.

The reactive derivatives of Compound (III) such as trifluoroacetic acid esters or compounds shown by a formula (IV):

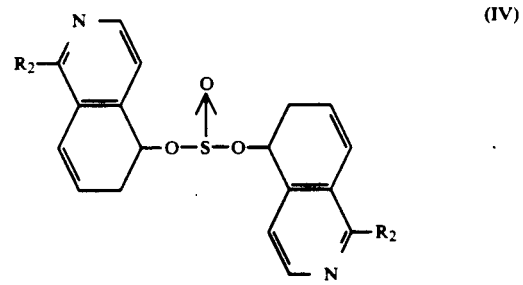

wherein $R_2$ is as hereinbefore defined, can be used.

As protecting groups of carboxy group in Compound (III), conventional ester groups such as benzyl, tertbutyl, trimethylsilyl and tetrahydropyranyl group may be illustrated.

For example, the protection by benzyl group is performed by the addition of benzyl halide such as benzyl chloride or benzyl bromide to 5-hydroxy-1-isoquinolinecarboxylic acid or potassium, sodium or tetramethylammonium salt thereof in a solvent and the reaction mixture is stirring in the presence or absence of a base such as potassium carbonate, sodium carbonate or triethylamine at −30° to 100° C. for a few hours to several days.

The solvent can be selected, according to the reaction conditions, from chloroform, dichloromethane, carbon tetrachloride, benzene, toluene, xylene, dioxane, tetrahydrofuran, acetonitrile, dimethylsulfoxide, dimethylformamide, ethyl acetate and hexamethylphosphoric triamide.

The protected 5-hydroxyisoquinoline compound is allowed to react with a 4-guanidinobenzoic acid or a reactive derivative thereof by one of said methods A-1 to A-3, and the protected isoquinolyl guanidinobenzoate can be obtained.

As a method of de-protection, catalytic reduction can be performed in a solution of the protected derivative in a solvent, e.g. methanol, ethanol and acetic acid, in the presence of palladium carbon under hydrogen gas atmosphere with stirring until no more hydrogen is absorbed.

Isolation and purification of the isoquinolyl guanidinobenzoate derivative (II) of the present invention can be performed by applying conventional chemical procedures, such as extraction, condensation, crystallization, filtration, recrystallization and various types of chromatography.

The obtained Compounds (II) of the present invention can be formed salts with acids by conventional methods.

Suitable examples of the acids are sulfuric acid, hydrochloric acid, nitric acid, phosphoric acid, hydrobromic acid, carbonic acid, formic acid, acetic acid, lactic acid, succinic acid, tartaric acid, malic acid, citric acid, methanesulfonic acid, p-toluenesulfonic acid and benzenesulfonic acid.

On the other hands, the compounds of formulae (V) and (VI):

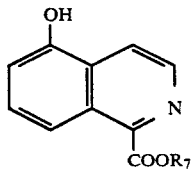 (V)

OH (VI)

wherein $R_7$ is a ($C_1$, $C_3$ or $C_4$) alkyl, phenyl, benzyl or —$CH_2CONR_5R_6$ group (wherein $R_5$ and $R_6$ are the same or different and selected from a hydrogen atom and ($C_1$–$C_4$) alkyl groups), are novel 5-hydroxy-1-isoquinolinecarboxylic acid esters can be obtained by the condensation of 5-hydroxy-1-isoquinolinecarboxylic acid and a Compound (VI).

The condensation can be performed by applying a conventional method.

METHOD B-1

Compounds (V) of the present invention can be prepared by a reaction of 5-hydroxy-1-isoquinolinecarboxylic acid or a salt thereof and a Compound (VI) thereof in the presence of a catalyst or a condensing agent.

Suitable examples of the catalysts are sulfuric acid, hydrochloric acid, p-toluenesulfonic acid, phosphorous oxychloride, polyphosphoric acid and boron trifluoride. Suitable examples of condensing agents are diphenylphosphorylazide, dicyclohexylcarbodiimide (DCC), N,N'-carbodiimidazole, N,N'-disuccinimidyl carbonate, 1-(3-dimethylaminopropyl)-3-ethylcarbodiimide, dimethylformamide diethylacetal, N,N'-dimethylphosphoramidic dichloride and phenyl dichlorophosphate. Additionally the basic catalysts, e.g. pyridine, triethylamine, diisopropylethylamine, di-tert-butylamine, dimethylaminopyridine, pyrrolidinopyridine, N-methylmorpholine and 1,8-diazabicyclo [5,4,0]-7-undecene may be used with above condensing agents.

As an example of method B-1, 5-hydroxy-1-isoquinolinecarboxylic acid is allowed to react in a Compound (VI) saturated with HCl gas. The reaction is carried out by heating for a few hours to several days.

METHOD B-2

Compounds (V) of the present invention can be prepared by a reaction of 5-hydroxy-1-isoquinolinecarboxylic acid or a salt thereof, and a reactive derivative of Compounds (VI) including alkyl halides shown by the formula (VII):

(wherein, X is chlorine, bromine or iodine atom), trifluoroacetic acid esters of Compound (VI) or compounds shown by the formula (VIII):

may be used.

The reaction condition varies with the properties of the reactive derivatives, for example an alkyl halide is reacted with an alkali metal salt of 5-hydroxy-1-isoquinolinecarboxylic acid in a solvent with stirring at −30° to 100° C. for a few hours to several days.

Isolation and purification of Compounds (V) from the reaction mixture can be performed by applying conventional chemical procedures such as extraction, condensation, crystallization, filtration, recrystallization and various types of chromatography. The obtained Compounds (V) of the present invention may be formed salts with acids by conventional methods, as required. Suitable examples of the acids are sulfuric acid, hydrochloric acid, nitric acid, phosphoric acid, hydrobromic acid, carbonic acid, acetic acid, lactic acid, succinic acid, tartaric acid, malic acid, citric acid, methanesulfonic acid, p-toluenesulfonic acid and benzenesulfonic acid.

The inhibitory activity on trypsin in vitro was determined by the methods of Muramatsu, et al. described in the Journal of Biochemistry, 58, 214 (1965). The concentration of compounds shown by the formula (II) which inhibits 50% of the hydrolysis of p-tosylarginine methyl ester (TAME) with 1.5 μg of trypsin or casein with 20 μg of trypsin, respectively, at 37° C. in 10 minutes are shown in Table 1.

Test compound numbers and chemical structures of the test compounds and control drugs (Gabexate mesylate and Camostat mesylate) are shown below:

| Compound No. | Chemical structure |
|---|---|
| ① | 5-Isoquinolyl 4-guanidinobenzoate dimethanesulfonate monohydrate |

| | -continued |
|---|---|
| | Chemical structure |

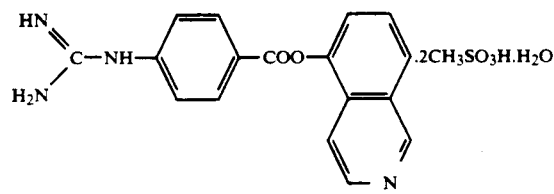

(2) 1'-Hydroxy-5'-isoquinolyl 4-guanidinobenzoate methanesulfonate

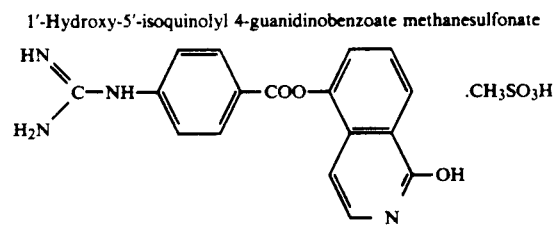

(3) 1'-Cyano-5'-isoquinolyl 4-guanidinobenzoate methanesulfonate monohydrate

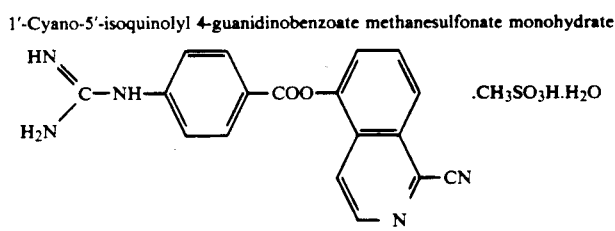

(4) 1'-Acetyl-5'-isoquinolyl 4-guanidinobenzoate hydrochloride

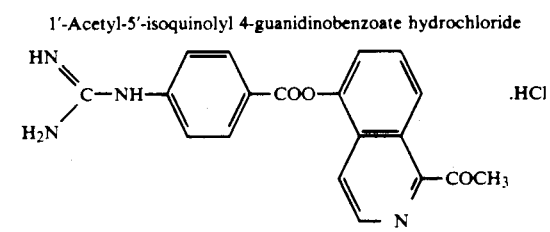

(5) 1'-Carboxy-5'-isoquinolyl 4-guanidinobenzoate quarterhydrate

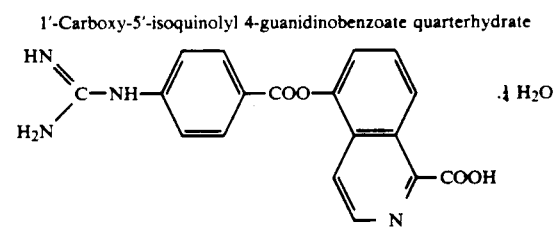

(6) 1'-Carbamoyl-5'-isoquinolyl 4-guanidinobenzoate methanesulfonate hemihydrate

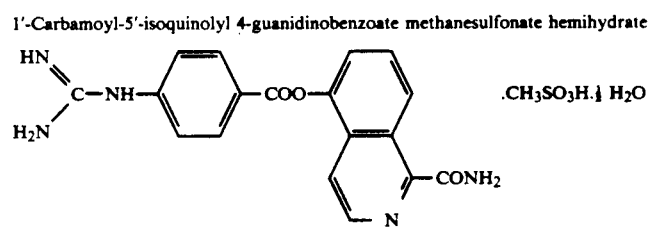

(7) 1'-Ethoxycarbonyl-5'-isoquinolyl 4-guanidinobenzoate hydrochloride

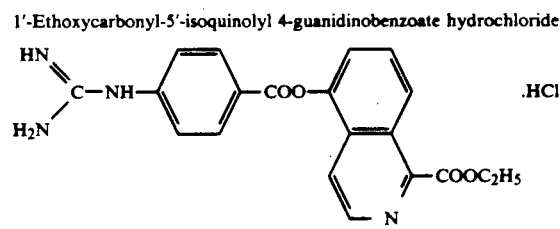

(8) 1'-Propoxycarbonyl-5'-isoquinolyl 4-guanidinobenzoate methanesulfonate

-continued

Chemical structure

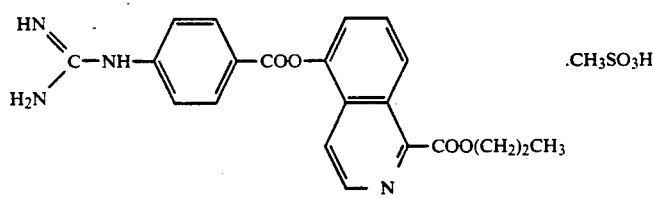

(9) 1'-Isopropoxycarbonyl-5'-isoquinolyl 4-guanidinobenzoate hydrochloride

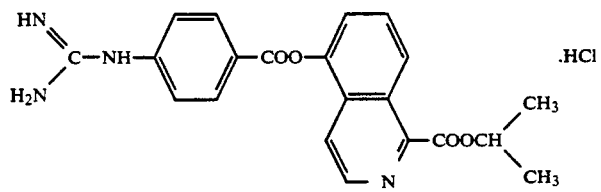

10 1'-Butoxycarbonyl-5'-isoquinolyl 4-guanidinobenzoate hydrochloride monohydrate

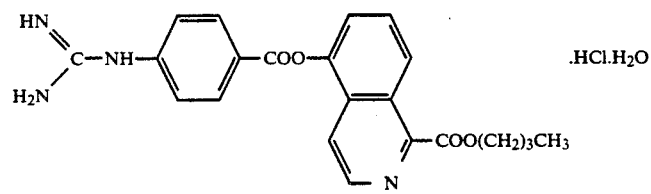

11 1'-Benzyloxycarbonyl-5'-isoquinolyl 4-guanidinobenzoate hydrochloride monohydrate

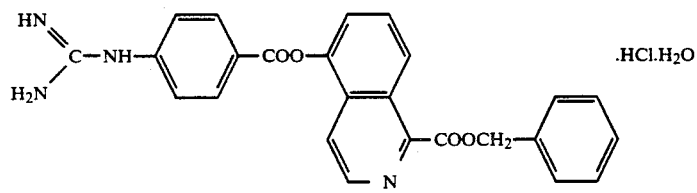

12 1'-(N,N-Dimethylcarbamoyl)methoxycarbonyl-5'-isoquinolyl 4-guanidinobenzoate hydrochloride

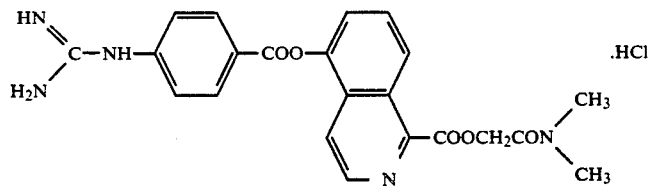

Control drugs (Gabexate mesylate)     Ethyl 4-(6-guanidinohexanoyloxy)benzoate methanesulfonate

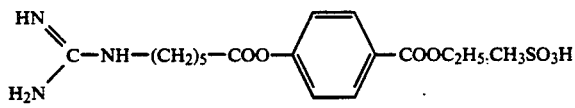

(Camostat mesylate)     N,N-Dimethylcarbamoylmethyl p-(p-guanidinobenzoyloxy)phenylacetate methanesulfonate

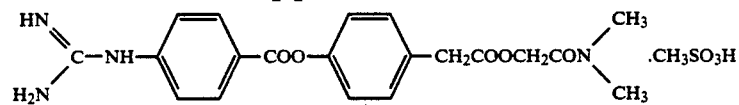

TABLE 1

| Compound No. | 50% inhibitory concentration (M) Substrate | |
|---|---|---|
| | TAME | Casein |
| ① | $5.6 \times 10^{-8}$ | $1.3 \times 10^{-7}$ |
| ② | $6.4 \times 10^{-8}$ | $1.4 \times 10^{-7}$ |
| ③ | $5.6 \times 10^{-8}$ | $1.4 \times 10^{-7}$ |
| ④ | $5.7 \times 10^{-8}$ | $1.4 \times 10^{-7}$ |
| ⑤ | $6.4 \times 10^{-8}$ | $1.7 \times 10^{-7}$ |
| ⑥ | $5.6 \times 10^{-8}$ | $1.6 \times 10^{-7}$ |

TABLE 1-continued

| Compound No. | 50% inhibitory concentration (M) Substrate | |
|---|---|---|
| | TAME | Casein |
| ⑦ | $5.6 \times 10^{-8}$ | $1.2 \times 10^{-7}$ |
| ⑧ | $9.6 \times 10^{-8}$ | $1.6 \times 10^{-7}$ |
| ⑨ | $1.3 \times 10^{-7}$ | $1.6 \times 10^{-7}$ |
| 10 | $1.5 \times 10^{-7}$ | $2.1 \times 10^{-7}$ |
| 11 | $3.4 \times 10^{-7}$ | $4.1 \times 10^{-7}$ |
| 12 | $6.6 \times 10^{-8}$ | $1.4 \times 10^{-7}$ |
| Gabexate mesylate | $1.5 \times 10^{-5}$ | $2.2 \times 10^{-6}$ |
| Camostat mesylate | $6.5 \times 10^{-8}$ | $1.4 \times 10^{-7}$ |

Note)
TAME: p-Tosylarginine methyl ester

As shown above, the isoquinolyl guanidinobenzoate derivatives (II) of the present invention possess excellent anti-trypsin activity and are useful for the treatment of disease caused by the activation of protease, for example, pancreatic diseases, hemorrhagic diseases and thrombosis.

The isoquinolyl guanidinobenzoate derivatives (II) of the present invention may take various suitable formations, such as tablets, capsules, granules, powders and injections with suitable additives, e.g. fillers, carriers or diluents and can be administered orally or parenterally.

The present invention is explained by the following examples, however, these examples are illustrative for the better understandings of the present invention and the present invention is not restricted by these examples.

EXAMPLE 1

Propyl 5-hydroxy-1-isoquinolinecarboxylate

Compound No. 13

The suspension of 3.00 g of 5-hydroxy-1-isoquinolinecarboxylic acid[1]) in 50 ml of 1-propanol saturated with HCl gas was heated under reflux for 25 hours.

The reaction mixture was concentrated under reduced pressure and the residue was placed in 50 ml of saturated aqueous sodium hydrogen carbonate and extracted three times with 100 ml of ethyl acetate. The combined extract was concentrated under reduced pressure and the residue was recrystallized from aqueous ethanol to give 1.48 g (yield 40.3%) of the title compound.

Melting point: 148°-150° C.
FAB-MS: 232 (M+H)+.
IR: $\nu^{KBr}$ cm$^{-1}$: 3430, 2970, 1720, 1585, 1460, 1265, 1170, 1120, 820, 740.

| | Elemental analysis for $C_{13}H_{13}NO_3$ | | |
|---|---|---|---|
| | C (%) | H (%) | N (%) |
| Calcd. | 67.52 | 5.67 | 6.06 |
| Found | 67.42 | 5.77 | 6.11 |

EXAMPLE 2

Isopropyl 5-hydroxy-1-isoquinolinecarboxylate

Compound No. 14

To a suspension of 2.51 g of 5-hydroxy-1-isoquinolinecarboxylic acid in 20 ml ethanol was added ethanolic potassium hydroxide (KOH 0.88 g, ethanol 20 ml). The solvent was removed under reduced pressure and the residue was suspended in 20 ml of dimethylformamide (DMF). To the suspension was added 2.26 g of 2-iodopropane and the mixture was stirred for one hour at 0° C. and 27 hours at room temperature.

The reaction mixture was poured into 200 ml of 5% aqueous sodium thiosulfate and extracted three times with 100 ml ethyl acetate. The combined extract was concentrated under reduced pressure and the residue was recrystallized from aqueous 2-propanol to give 1.36 g (yield 44.2%) of the title compound.

Melting point: 182°-183° C.
EI-MS: 231 M+.
IR: $\nu^{KBr}$ cm$^{-1}$: 3450, 2980, 1725, 1585, 1460, 1370, 1270, 1170, 1105, 930, 820, 740.

| | Elemental analysis for $C_{13}H_{13}NO_3$ | | |
|---|---|---|---|
| | C (%) | H (%) | N (%) |
| Calcd. | 67.52 | 5.67 | 6.06 |
| Found | 67.32 | 5.62 | 5.96 |

EXAMPLE 3

Butyl 5-hydroxy-1-isoquinolinecarboxylate

Compound No. 15

According to the method of example 2, 3.00 g of 5-hydroxy-1-isoquinolinecarboxylic acid, 1.05 g of potassium hydroxide and 11.6 g of 1-iodobutane were reacted and purified to give 0.54 g (yield 13.9%) of the title compound.

Melting point: 148°-150° C.
EI-MS: 245 M+.
IR: $\nu^{KBr}$ cm$^{-1}$: 2950, 2570, 1720, 1580, 1450, 1255, 1170, 1120, 825, 750, 570.

| | Elemental analysis for $C_{14}H_{15}NO_3$ | | |
|---|---|---|---|
| | C (%) | H (%) | N (%) |
| Calcd. | 68.84 | 5.78 | 5.73 |
| Found | 68.79 | 6.19 | 5.68 |

EXAMPLE 4

Benzyl 5-hydroxy-1-isoquinolinecarboxylate

Compound No. 16

According to the method of example 2, 3.00 g of 5-hydroxy-1-isoquinolinecarboxylic acid, 1.05 g of potassium hydroxide and 4.16 g of benzyliodide were reacted and purified to give 1.14 g (yield 25.7%) of the title compound.

Melting point: 164°-166° C.
EI-MS: 279 M+.
IR: $\nu^{KBr}$ cm$^{-1}$: 3430, 3040, 2950, 1720, 1580, 1460, 1370, 1260, 1170, 1120, 950, 820, 750, 695, 565.

| | Elemental analysis for $C_{17}H_{13}NO_3$ | | |
|---|---|---|---|
| | C (%) | H (%) | N (%) |
| Calcd. | 73.84 | 4.69 | 5.02 |
| Found | 73.00 | 4.78 | 5.07 |

EXAMPLE 5

N,N-Dimethylcarbamoylmethyl 5-hydroxy-1-isoquinolinecarboxylate

Compound No. 17

According to the method of example 2, 3.00 g of 5-hydroxy-1-isoquinolinecarboxylic acid, 1.05 g of potassium hydroxide and 3.00 g of α-bromo-N,N-dimethylacetamide were reacted and purified to give 2.20 g (yield 50.6%) of the title compound.

Melting point: 205°-208° C.
EI-MS: 274 M+.
IR: $\nu^{KBr}$ cm$^{-1}$: 3150, 1720, 1650, 1260, 1160, 1120, 815.

| | Elemental analysis for $C_{14}H_{14}N_2O_4$ | | |
|---|---|---|---|
| | C (%) | H (%) | N (%) |
| Calcd. | 61.31 | 5.14 | 10.21 |
| Found | 61.11 | 5.34 | 10.11 |

EXAMPLE 6

1-Acetyl-5-hydroxyisoquinoline

Compound No. 18

To a suspension of 3.85 g of sodium ethylate in 50 ml of toluene was added 803 mg of ethyl 5-hydroxy-1-isoquinolinecarboxylate[1] followed by 10.6 ml of ethyl acetate. The mixture was heated on the steam-bath with stirring for four hours. To the cooled reaction mixture was added 20 ml of water followed by 27 ml of six normal hydrochloric acid, and the mixture was stirred thoroughly to extract the β-keto ester from the toluene layer. The aqueous layer was heated under reflux for one hour and the solution was made alkaline with saturated aqueous potassium carbonate and extracted five times with 50 ml of ethyl acetate. The extract was concentrated under reduced pressure to give the precipitates, which were purified by silica gel column chromatography using, as eluent, a mixed solvent of hexane:ethyl acetate=3:1 to give 430 mg (yield 63.1%) of the title compound.

Melting point: 149°-152° C.
FAB-MS: 188 (M+H)+.
IR: $\nu^{KBr}$ cm$^{-1}$: 3430, 1695, 1585, 1255.

| | Elemental analysis for $C_{11}H_9NO_2$ | | |
|---|---|---|---|
| | C (%) | H (%) | N (%) |
| Calcd. | 70.53 | 4.85 | 7.48 |
| Found | 70.55 | 4.92 | 7.36 |

EXAMPLE 7

5-Hydroxy-1-isoquinolinecarboxamide

Compound 19

The suspension of 3.00 g of 1-cyano-5-benzoyloxyisoquinoline[1] in 50 ml of methanol saturated with HCl gas was stirred at room temperature for 20 hours. The precipitates were collected by filtration and suspended in 50 ml of methanol.

The mixture was heated at 50° C. for three hours and concentrated under reduced pressure. The residue was mixed with saturated aqueous sodium hydrogen carbonate and the formed precipitates were collected and washed with water and acetone successively. The precipitates were recrystallized from acetone to give 650 mg (yield 31.7%) of the title compound.

Melting point: 222°-225° C.
EI-MS: 188 M+.
IR: $\nu^{KBr}$ cm$^{-1}$: 3400, 3130, 1670, 1590, 1460, 1395, 1340, 1275, 820.

| | Elemental analysis for $C_{11}H_9NO_2$ | | |
|---|---|---|---|
| | C (%) | H (%) | N (%) |
| Calcd. | 63.78 | 4.23 | 14.94 |
| Found | 63.50 | 4.43 | 14.93 |

EXAMPLE 8

5-Isoquinolyl 4-guanidinobenzoate dimethanesulfonate monohydrate

Compound No. ①

To a chilled solution of 3.51 g of 4-guanidinobenzoic acid hydrochloride in 60 ml of pyridine was added 4.25 g of dicyclohexylcarbodiimide (DCC) and the mixture was stirred for one hour at 0° C. Then a solution of 2.37 g of 5-hydroxyisoquinoline[1] in 30 ml of pyridine was added to this reaction mixture over 30 minutes period, and stirred for another one hour. A reaction mixture was gradually raised to room temperature and stirred for 20 hours.

The precipitated crystals were collected by filtration, washed with pyridine and acetone successively. The crystals were dissolved in 100 ml of methanol and the insoluble materials were filtered off. The filtrate was concentrated under reduced pressure to give 2.61 g of residue, which was purified by silica gel column chromatography using, as eluent, a mixed solvent of $CHCl_3$:$CH_3OH$:$CH_3COOH$=10:1:1, to give 2.54 g of the acetate.

The acetate was suspended in ethanol and methanesulfonic acid was added to this suspension to make a clear solution. To the solution, 100 ml of ether was added and the formed crystals were collected. The crystals were recrystallized from ethanol to give 2.63 g (yield 31.3%) of the title compound.

Melting point: 182°-184° C.
FAB-MS: 307 (M+H)+, 399 (M+Gly+H)+.
IR: $\nu^{KBr}$ cm$^{-1}$: 3340, 3130, 1730, 1695, 1650, 1615, 1575, 1265, 1240, 1210, 1100, 1040, 840, 775, 540.

| | Elemental analysis for $C_{17}H_{14}N_4O_2 \cdot 2CH_3SO_3H \cdot H_2O$ | | | |
|---|---|---|---|---|
| | C (%) | H (%) | N (%) | S (%) |
| Calcd. | 44.18 | 4.68 | 10.85 | 12.41 |
| Found | 44.10 | 4.53 | 10.97 | 12.72 |

EXAMPLE 9

1'-Hydroxy-5'-isoquinolyl 4-guanidinobenzoate methanesulfonate

Compound No. ②

According to the method of example 8, 2.70 g of 4-guanidinobenzoic acid hydrochloride, 2.60 g of DCC and 2.00 g of 1,5-isoquinolinediol[1] were reacted.

The precipitates were collected by filtration and suspended in methanol and methanesulfonic acid was added to this suspension. The insoluble materials were filtered off and the filtrate was concentrated under reduced pressure to give crystals, which were recrystallized from methanol to give 0.10 g (yield 2.0%) of the title compound.

Melting point: 209°–213° C.
FAB-MS: 323 (M+H)+.
IR: $\nu^{KBr}$ cm$^{-1}$: 3400, 3200, 1740, 1700, 1660, 1640, 1610, 1570, 1515, 1480, 1400, 1265, 1230, 1170, 1040, 740.

Elemental analysis for $C_{17}H_{14}N_4O_3 \cdot CH_3SO_3H$

|  | C (%) | H (%) | N (%) | S (%) |
| --- | --- | --- | --- | --- |
| Calcd. | 51.67 | 4.34 | 13.39 | 7.66 |
| Found | 51.51 | 4.27 | 13.31 | 7.74 |

EXAMPLE 10

1′-Cyano-5′-isoquinolyl 4-guanidinobenzoate methanesulfonate monohydrate

Compound No. ③

According to the method of example 8, 0.65 g of 4-guanidinobenzoic acid hydrochloride, 0.78 g of DCC and 0.51 g of 1-cyano-5-hydroxyisoquinoline[1] were reacted.

The reaction mixture was filtered and the filtrate was concentrated under reduced pressure. The condensed solution was mixed with 30 ml of saturated aqueous sodium hydrogen carbonate and the formed precipitates were collected and washed with water and acetone successively to give 1.17 g of the carbonate.

The carbonate was suspended in nine ml of DMF and dissolved by addition of 0.69 g of methanesulfonic acid and 30 ml of ether was added to the solution.

The resulting crystals were collected and recrystallized from methanol to give 0.30 g (yield 22.3%) of the title compound.

Melting point: 220°–225° C.
FAB-MS: 332 (M+H)+.
IR: $\nu^{KBr}$ cm$^{-1}$: 3370, 3180, 2240, 1745, 1685, 1605, 1580, 1415, 1400, 1255, 1200, 1175, 1145, 1060, 760.

Elemental analysis for $C_{18}H_{13}N_5O_2 \cdot CH_3SO_3H \cdot H_2O$

|  | C (%) | H (%) | N (%) | S (%) |
| --- | --- | --- | --- | --- |
| Calcd. | 51.23 | 4.30 | 15.72 | 7.20 |
| Found | 51.37 | 4.04 | 15.77 | 7.43 |

EXAMPLE 11

1′-Acetyl-5′-isoquinolyl 4-guanidinobenzoate hydrochloride

Compound No. ④

According to the method of example 10, 0.70 g of 4-guanidinobenzoic acid hydrochloride, 0.67 g of DCC and 0.61 g of 1-acetyl-5-hydroxyisoquinoline, prepared by the method of example 6, were reacted and worked-up to give 0.77 g of the carbonate.

The carbonate was purified by silica gel column chromatography using, as eluent, a mixed solvent of $CHCl_3:CH_3OH:CH_3COOH=10:1:1$ to give the acetate. The acetate was suspended in 2-propanol and dissolved by addition of hydrochloric acid and this solution was concentrated under reduced pressure to give the hydrochloride. The hydrochloride was recrystallized from 2-propanol to give 0.17 g (yield 13.3%) of the title compound.

Melting point: 210°–211° C. (dec.).
FAB-MS: 350 (M+H)+,
IR: $\nu^{KBr}$ cm$^{-1}$: 3430, 3100, 1740, 1690, 1235.

Elemental analysis for $C_{19}H_{16}N_4O_3 \cdot HCl$

|  | C (%) | H (%) | N (%) |
| --- | --- | --- | --- |
| Calcd. | 59.30 | 4.45 | 14.56 |
| Found | 59.06 | 4.59 | 14.34 |

EXAMPLE 12

1′-Carboxy-5′-isoquinolyl 4-guanidinobenzoate quarterhydrate

Compound No. ⑤

According to the method of example 8, 3.88 g of 4-guanidinobenzoic acid hydrochloride, 4.30 g of DCC and 5.30 g of benzyl 5-hydroxy-1-isoquinolinecarboxylate prepared by the method of example 4 were reacted.

The reaction mixture was filtered and 400 ml of ether was added to the filtrate to form precipitates which were recrystallized from 150 ml of ethanol to give 3.65 g of 1′-benzyloxycarbonyl-5′-isoquinolyl 4-guanidinobenzoate hydrochloride monohydrate (melting point: 112°–113° C.).

The mixture of 3.50 g of the above mentioned compound and 0.30 g of 5% palladium carbon in 50 ml of methanol were stirred in hydrogen gas atmosphere for 20 hours at room temperature. One hundred ml of acetic acid was added to this reaction mixture and the insoluble materials were filtered off and the solvent was removed under reduced pressure. The residue was recrystallized from 300 ml of 50% methyl cellosolve to give 1.03 g (yield 16.8%) of the title compound.

Melting point: 225°–235° C. (dec.),
FAB-MS: 351 (M+H)+,
IR: $\nu^{KBr}$ cm$^{-1}$: 3450, 3150, 1730, 1700, 1610, 1555, 1405, 1275, 1240, 1230, 1070, 820, 760.

Elemental analysis for $C_{18}H_{14}N_4O_4 \cdot \frac{1}{4}H_2O$

|  | C (%) | H (%) | N (%) |
| --- | --- | --- | --- |
| Calcd. | 60.93 | 4.12 | 15.79 |
| Found | 60.79 | 3.97 | 15.62 |

EXAMPLE 13

1′-Carbamoyl-5′-isoquinolyl 4-guanidinobenzoate methanesulfonate hemihydrate

Compound No. ⑥

According to the method of example 8, 0.55 g of 4-guanidinobenzoic acid hydrochloride, 0.53 g of DCC and 0.48 g of 5-hydroxy-1-isoquinolinecarboxamide, prepared by the method of example 7, were reacted.

The reaction mixture was filtered, the filtrate was mixed with 400 ml of ether to form an oily residue.

The oily residue was purified by silica gel column chromatography using, as eluent, a mixed solvent of $CHCl_3: CH_3OH: CH_3COOH=10:3:1$. The obtained residue was dissolved in methanol and mixed with a saturated aqueous sodium hydrogen carbonate and formed precipitates were collected and washed with water and acetone successively to give the carbonate.

The carbonate was suspended in methanol and a methanesulfonic acid was added dropwise to make the suspension acidic. The insoluble materials were filtered off and the filtrate was allowed to stand to give 0.18 g (yield 20.0%) of the title compound.

Melting point: 264°–268° C. (dec.),
FAB-MS: 350 (M+H)+,
IR: $\nu^{KBr}$ cm$^{-1}$: 3420, 3170, 1730, 1680, 1575, 1520, 1410, 1275, 1240, 1225, 1165, 1040, 765, 620.

| Elemental analysis for $C_{18}H_{15}N_5O_3 \cdot CH_3SO_3H \cdot \frac{1}{2}H_2O$ | | | | |
|---|---|---|---|---|
| | C (%) | H (%) | N (%) | S (%) |
| Calcd. | 50.22 | 4.44 | 15.41 | 7.06 |
| Found | 50.65 | 4.49 | 15.32 | 6.88 |

EXAMPLE 14

1'-Ethoxycarbonyl-5'-isoquinolyl 4-guanidinobenzoate hydrochloride

Compound No. ⑦

According to the method of example 10, 5.00 g of 4-guanidinobenzoic acid hydrochloride, 4.70 g of DCC and 5.00 g of ethyl 5-hydroxy-1-isoquinolinecarboxylate[1] were reacted to give 6.40 g of the carbonate. To the suspension of the carbonate in 100 ml of methanol was added seven ml of methanol saturated with HCl gas and the insoluble materials were filtered off. The filtrate was concentrated under reduced pressure to give a corresponding crude hydrochloride and recrystallized from ethanol to give 0.84 g (yield 8.7%) of the title compound.

Melting point: 187°–192° C.
FAB-MS: 470 (M+Gly+H)+.
IR: $\nu^{KBr}$ cm$^{-1}$: 3300, 2980, 1730, 1680, 1630, 1600, 1570, 1510, 1460, 1270, 1230, 1160, 1060, 1010, 760.

| Elemental analysis for $C_{20}H_{18}N_4O_4 \cdot HCl$ | | | |
|---|---|---|---|
| | C (%) | H (%) | N (%) |
| Calcd. | 57.91 | 4.62 | 13.51 |
| Found | 57.46 | 4.73 | 13.72 |

EXAMPLE 15

1'-Propoxycarbonyl-5'-isoquinolyl 4-guanidinobenzoate methanesulfonate

Compound No. ⑧

According to the method of example 8, 1.08 g of 4-guanidinobenzoic acid hydrochloride, 1.03 g of DCC and 1.16 g of propyl 5-hydroxy-1-isoquinolinecarboxylate, prepared by the method of example 1, were reacted to give 1.71 g of the carbonate.

By the same method of example 11, the carbonate was converted to 0.98 g (yield 40.8%) of the title compound.

Melting point: 175°–177° C.
FAB-MS: 393 (M+H)30.
IR: $\nu^{KBr}$ cm$^{-1}$: 3300, 3200, 1740, 1700, 1575, 1235, 1210, 1170, 1050.

| Elemental analysis for $C_{21}H_{20}N_4O_4 \cdot CH_3SO_3H$ | | | | |
|---|---|---|---|---|
| | C (%) | H (%) | N (%) | S (%) |
| Calcd. | 54.09 | 4.95 | 11.47 | 6.56 |
| Found | 54.03 | 5.00 | 11.45 | 6.73 |

EXAMPLE 16

1'-Isopropoxycarbonyl-5'-isoquinolyl 4-guanidinobenzoate hydrochloride

Compound No. ⑨

According to the method of example 8, 1.40 g of 4-granidinobenzoic acid hydrochloride, 1.55 g of DCC and 1.50 g of isopropyl 5-hydroxy-1-isoquinolinecarboxylate, prepared by the method of example 2, were reacted. The reaction mixture was mixed with 50 ml of ether to give crystals which were recrystallized from ethanol-ether to give 1.51 g (yield 54.2%) of the title compound.

Melting point: 177°–180° C.
FAB-MS: 393 (M+H)30.
IR: $\nu^{KBr}$ cm$^{-1}$: 3500, 2980, 1730, 1680, 1625, 1600, 1570, 1270, 1230, 1170, 1065, 760, 745.

| Elemental analysis for $C_{21}H_{20}N_4O_4 \cdot HCl$ | | | |
|---|---|---|---|
| | C (%) | H (%) | N (%) |
| Calcd. | 58.81 | 4.94 | 13.06 |
| Found | 58.63 | 4.99 | 12.96 |

EXAMPLE 17

1'-Butoxycarbonyl-5'-isoquinolyl 4-guandinobenzoate hydrochloride monohydrate

Compound No. 10

According to the method of example 8, 0.88 g of 4-guanidinobenzoic acid hydrochloride, 0.84 g of DCC and 1.00 g of butyl 5-hydroxy-1-isoquinolinecarboxylate, prepared by the method of example 3, were reacted. The reaction mixture was filtered and the filtrate was mixed with 60 ml of ether to give precipitates. The precipitates were purified by silica gel column chromatography using, as eluent, a mixed solvent of $CHCl_3:CH_3OH:CH_3COOH = 10:1:1$. The solvent was removed under reduced pressure and the residue was triturated with acetone to give 0.30 g (yield 16.2%) of the title compound.

Melting point: 162°–171° C.
FAB-MS: 407 (M+H)30.
IR: $\nu^{KBr}$ cm$^{-1}$: 3310, 2960, 1730, 1680, 1570, 1270, 1230, 1165, 1060, 760.

| Elemental analysis for $C_{22}H_{22}N_4O_4 \cdot HCl \cdot H_2O$ | | | |
|---|---|---|---|
| | C (%) | H (%) | N (%) |
| Calcd. | 57.33 | 5.47 | 12.16 |
| Found | 57.19 | 5.24 | 11.97 |

EXAMPLE 18

1'-Benzyloxycarbonyl-5'-isoquinolyl 4-guanidinobenzoate hydrochloride monohydrate Compound No. 11

According to the method of example 12, 0.77 g of 4-guanidinobenzoic acid hydrochloride, 0.86 g of DCC and 1.00 g of benzyl 5-hydroxy-1-isoquinolinecarboxylate, prepared by the method of example 4, were reacted and obtained 0.87 g (yield 49.1%) of the title compound.

Melting point: 112°–113° C.
FAB-MS: 441 (M+H)+

IR: $\nu^{KBr}$ cm$^{-1}$: 3370, 3150, 1740, 1680, 1600, 1575, 1275, 1230, 1170, 1060, 1020, 760, 750, 700.

| Elemental analysis for $C_{25}H_{20}N_4O_4 \cdot HCl \cdot H_2O$ | | | |
|---|---|---|---|
| | C (%) | H (%) | N (%) |
| Calcd. | 60.67 | 4.68 | 11.32 |
| Found | 60.68 | 4.80 | 11.55 |

EXAMPLE 19

1'-(N,N-dimethylcarbamoyl)methyloxycarbonyl-5'-isoquinolyl 4-guanidinobenzoate hydrochloride Compound No. 12

According to the method of example 11, 1.00 g of 4-guanidinobenzoic acid hydrochloride, 1.00 g of DCC and 1.40 g of N,N-dimethylcarbamoylmethyl 5-hydroxy-1-isoquinolinecarboxylate, prepared by the method of example 5, were reacted and worked-up to give 1.36 g (yield 62.1%) of the title compound.

Melting point: 184°–187° C.
FAB-MS: 436 (M+H)$^+$.
IR: $\nu^{KBr}$ cm$^{-1}$: 3280, 3150, 1760, 1740, 1670, 1600, 1570, 1510, 1170, 1150, 1120, 1050, 820.

| Elemental analysis for $C_{22}H_{21}N_5O_5 \cdot HCl$ | | | |
|---|---|---|---|
| | C (%) | H (%) | N (%) |
| Calcd. | 56.00 | 4.70 | 14.84 |
| Found | 56.19 | 4.62 | 14.46 |

REFERENCE

1) V. Georgian et al., J. Org. Chem., 27, 4571 (1962).

Figure 1:
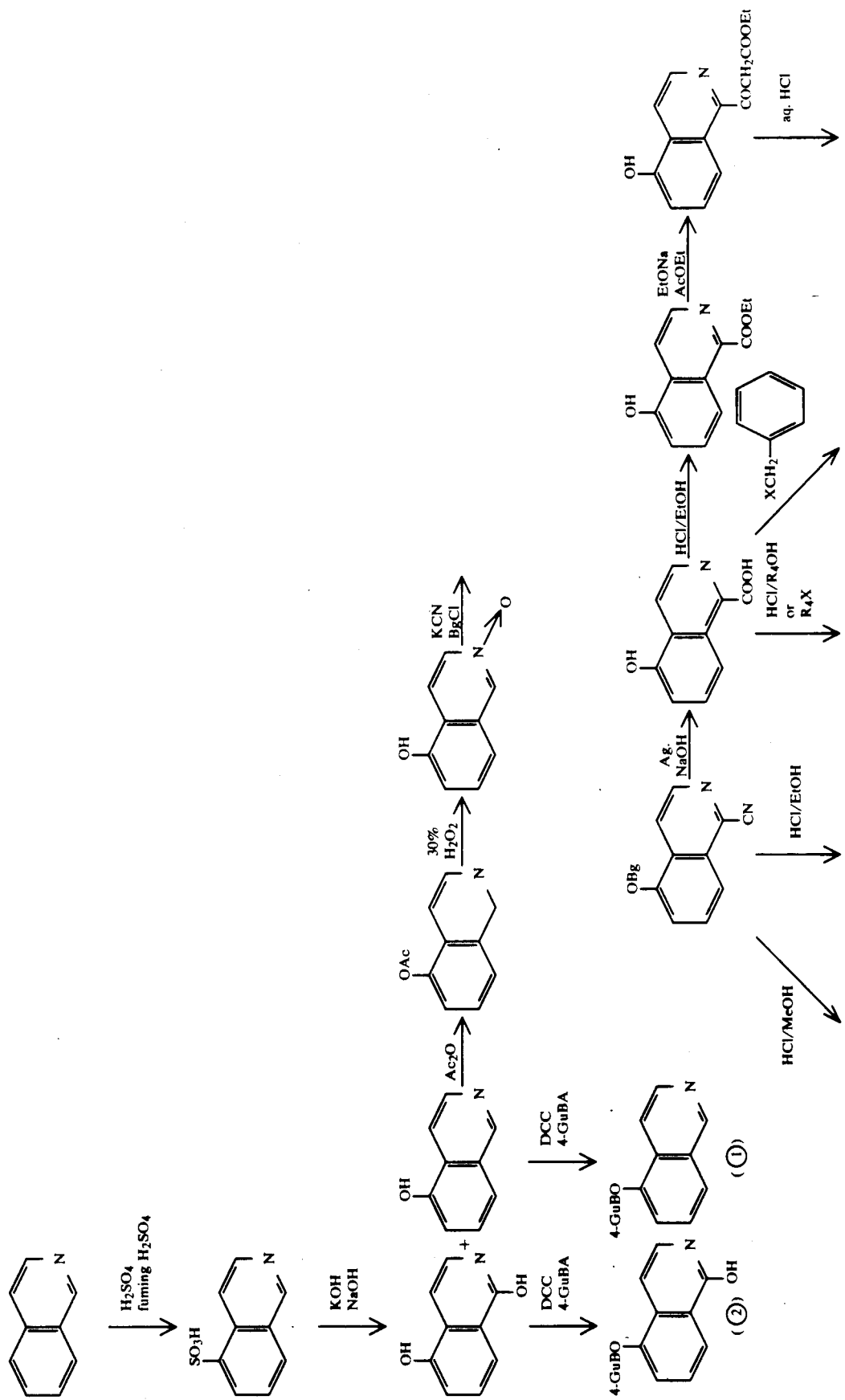
FIG. 1 shows schema for the synthesis of isoquinoline derivatives of the present invention. The numerals in the parentheses show the compound Nos. is isoquinoline derivatives of the present invention.
Figure 1:
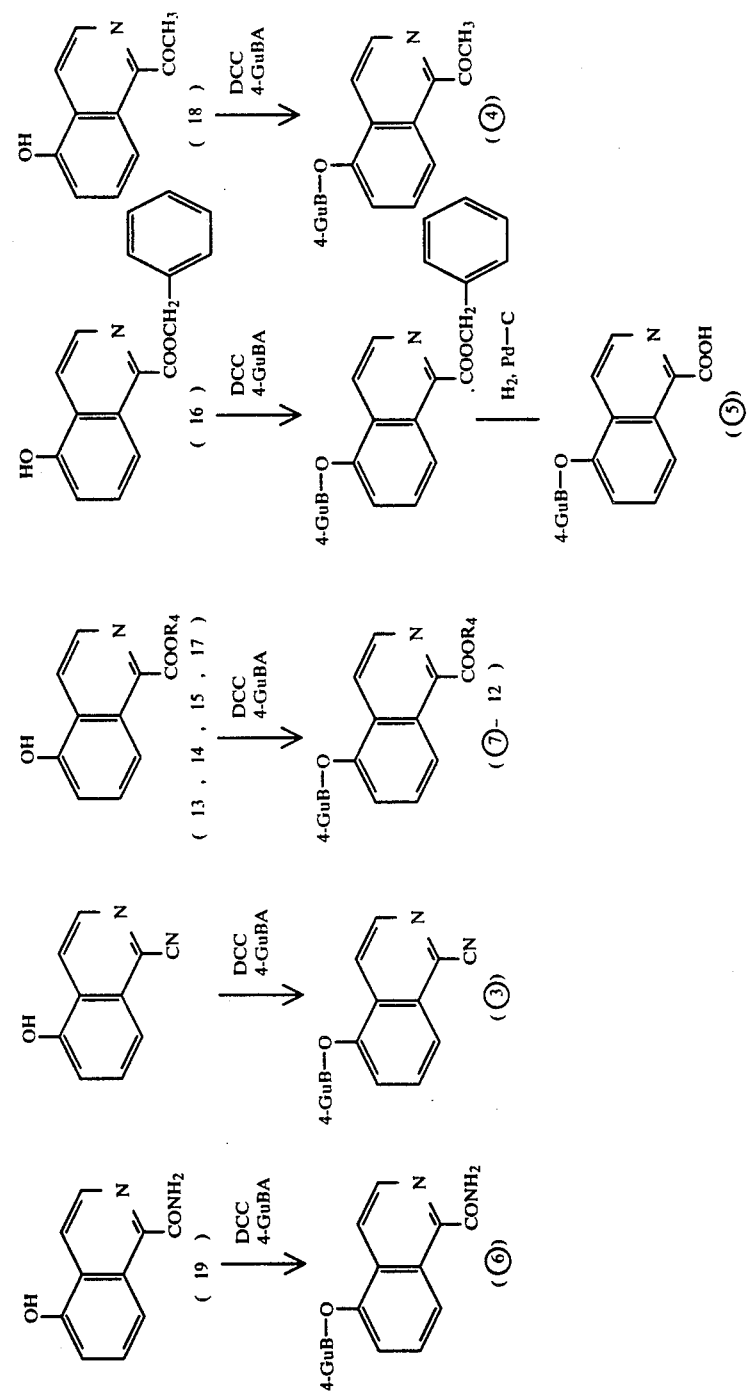
Figure 1:
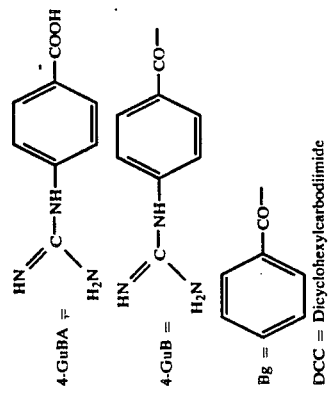

We Claim:

1. A compound of Formula (I)

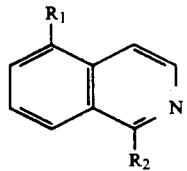

and pharmaceutically acceptable salts thereof, wherein R$_1$ is

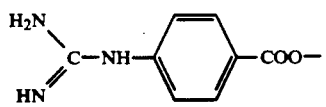

and R$_2$ is selected from the group consisting of a hydrogen atom, hydroxy, cyano, a —COR$_3$ group (wherein R$_3$ is an amino or (C$_1$–C$_4$) alkyl group) or a —COOR$_4$ group (wherein R$_4$ is a hydrogen atom, a (C$_1$–C$_4$) alkyl group, phenyl, or benzyl) or a —CH$_2$CONR$_5$R$_6$ group (wherein R$_5$ and R$_6$ are the same or different and are selected from a hydrogen atom and a (C$_1$–C$_4$) alkyl group).

2. The isoquinoline derivative of claim 1 which is 5-isoquinolyl 4-guanidinobenzoate and pharmaceutically acceptable salts thereof.

3. The isoquinoline derivative of claim 1 which is 1'-hydroxy-5'-isoquinolyl 4-guanidinobenzoate and pharmaceutically acceptable salts thereof.

4. The isoquinoline derivative of claim 1 which is 1'-cyano-5'-isoquinolyl 4-guanidinobenzoate and pharmaceutically acceptable salts thereof.

5. The isoquinoline derivative of claim 1 which is 1'-acetyl-5'-isoquinolyl 4-guanidinobenzoate and pharmaceutically acceptable salts thereof.

6. The isoquinoline derivative of claim 1 which is 1'-carboxy-5'-isoquinolyl 4-guanidinobenzoate and pharmaceutically acceptable salts thereof.

7. The isoquinoline derivative of claim 1 which is 1'-carbamoyl-5'-isoquinolyl 4-guanidinobenzoate and pharmaceutically acceptable salts thereof.

8. The isoquinoline derivative of claim 1 which is 1'-ethoxycarbonyl-5'-isoquinolyl 4-guanidinobenzoate and pharmaceutically acceptable salts thereof.

9. The isoquinoline derivative of claim 1 which is 1'-propoxycarbonyl-5'-isoquinolyl 4-guanidinobenzoate and pharmaceutically acceptable salts thereof.

10. The isoquinoline derivative of claim 1 which is 1'-isopropoxycarbonyl-5'-isoquinolyl 4-guanidinobenzoate and pharmaceutically acceptable salts thereof.

11. The isoquinoline derivative of claim 1 which is 1'-butoxycarbonyl-5'-isoquinolyl 4-guanidinobenzoate and pharmaceutically acceptable salts thereof.

12. The isoquinoline derivative of claim 1 which is 1'-benzyloxycarbonyl-5'-isoquinolyl 4-guanidinobenzoate and pharmaceutically acceptable salts thereof.

13. The isoquinoline derivative of claim 1 which is 1'-(N,N-dimethylcarbamoyl)methyloxycarbonyl-5'-isoquinolyl 4-guanidinobenzoate and pharmaceutically acceptable salts thereof.

14. Isoquinoline derivatives having the following Formula (III)

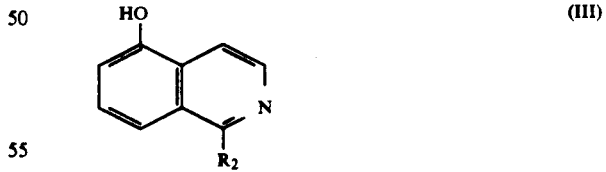

and pharmaceutically acceptable salts thereof, wherein R$_2$ is selected from the group consisting of a —COR$_3$ group wherein R$_3$ is an amino or C$_1$–C$_4$ alkyl group, and a —COOR$_4$ group wherein R$_4$ is a C$_1$, C$_3$ or C$_4$ alkyl, phenyl, benzyl or a —CH$_2$CONR$_5$R$_6$ group, wherein R$_5$ and R$_6$ are the same or different and are selected from hydrogen and C$_1$–C$_4$ alkyl groups.

15. The isoquinoline derivatives of claim 14 having the following Formula (V) and pharmaceutically acceptable salts thereof:

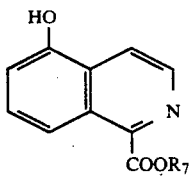

(V)

wherein, $R_7$ is a $C_1$, $C_3$ or $C_4$ alkyl group, phenyl, benzyl or a —$CH_2CONR_5R_6$ group.

16. The isoquinoline derivative of claim 15 which is propyl 5-hydroxy-1-isoquinolinecarboxylate and pharmaceutically acceptable salts thereof.

17. The isoquinoline derivative of claim 15 which is isopropyl 5-hydroxy-1-isoquinolinecarboxylate and pharmaceutically acceptable salts thereof.

18. The isoquinoline derivative of claim 15 which is butyl 5-hydroxy-1-isoquinolinecarboxylate and pharmaceutically acceptable salts thereof.

19. The isoquinoline derivative of claim 15 which is benzyl 5-hydroxy-1-isoquinolinecarboxylate and pharmaceutically acceptable salts thereof.

20. The isoquinoline derivative of claim 15 which is N,N-dimethylcarbamoylmethyl 5-hydroxy-1-isoquinolinecarboxylate and pharmaceutically acceptable salts thereof.

* * * * *